(12) United States Patent
Kamran

(10) Patent No.: US 8,398,684 B2
(45) Date of Patent: Mar. 19, 2013

(54) BONE ANCHORING MEMBER

(76) Inventor: Aflatoon Kamran, Corona del Mar, CA (US)

(\*) Notice: Subject to any disclaimer, the term of this patent is extended or adjusted under 35 U.S.C. 154(b) by 337 days.

(21) Appl. No.: 12/462,127

(22) Filed: Jul. 29, 2009

(65) Prior Publication Data

US 2010/0042165 A1  Feb. 18, 2010

Related U.S. Application Data

(60) Provisional application No. 61/137,255, filed on Jul. 29, 2008.

(51) Int. Cl.
*A61B 17/70* (2006.01)

(52) U.S. Cl. .......... 606/267; 606/265; 606/264; 606/246

(58) Field of Classification Search .......... 606/246–279, 606/305–308
See application file for complete search history.

(56) References Cited

U.S. PATENT DOCUMENTS

| 5,584,831 | A  | * | 12/1996 | McKay ................. 606/86 A |
| 6,231,575 | B1 | * | 5/2001  | Krag ................... 606/264 |
| 6,699,248 | B2 | * | 3/2004  | Jackson ................ 606/300 |
| 2005/0171538 | A1 | * | 8/2005 | Sgier et al. ............. 606/61 |
| 2008/0312696 | A1 | * | 12/2008 | Butters et al. ......... 606/264 |

\* cited by examiner

*Primary Examiner* — Eduardo C Robert
*Assistant Examiner* — Nicholas Plionis
(74) *Attorney, Agent, or Firm* — Ober, Kaler, Grimes & Shriver; Royla W. Craig; Christopher F. Lonegro

(57) ABSTRACT

A threaded rod or pedicle screw for insertion into the pedicle portion of a vertebra and having at its exposed end a second threaded rod rigidly connected in a generally parallel orientation to the longitudinal axis of the pedicle screw. The second rod being offset from the longitudinal axis of the pedicle screw and having a locking pin or arm and retaining nut for affixing a rod to the pedicle screw substantially over and aligned with the longitudinal axis of the pedicle screw.

11 Claims, 4 Drawing Sheets

BONE ANCHORING MEMBER

CROSS-REFERENCE TO RELATED APPLICATIONS

The present application derives priority from provisional application 61/137,255 filed on Jul. 29, 2008 which is incorporated herein by reference.

BACKGROUND OF THE INVENTION

1. Field of the invention

The present invention relates generally to devices and methods for treating spinal disorders and more specifically to a fixation assembly for retaining vertebrate endoskeletal members in a desired fixed spatial relationship.

2. Description of the Background

A variety of devices are known for the fixation of endoskeletal members or bones in humans and animals. Fixation of bones may be temporary in order to allow for normal healing, as with a break in the long bones of the limbs, or permanent in order to provide support and alignment of the skeletal members. The latter is often the case with respect to the vertebrae of a spinal column where support and spatial fixation are necessary due to injury or disease. Even where vertebral or spinal healing occurs after fixation, the fixations means or devices, which include bone fastener assemblies, often remain in position for life.

Bone fastener assemblies utilized in conjunction with spinal fixation often include a pedicle screw assembly or assemblies that are anchored by threaded engagement into the pedicle of each of the vertebrae that are to be maintained in a desired spatial relationship. One or more longitudinal supports, which may comprise plates or rods that extend generally longitudinally along the spinal column, are connected securely to the pedicle screw assemblies in a manner that allows the vertebrae to be maintained in a desired alignment. In order to achieve the desired stability, the bone fasteners must be attached securely to the vertebrae and connected firmly to the appliance.

A variety of means have been utilized to connect the rods or plates to the pedicle screws or other bone fasteners. The secure placement and alignment of a rod between pedicle screws or the placement of a plate linking two or more rigid screws can be difficult due to the angular orientation of the screws and exacerbated by any deformity of the spinal column. Precise alignment with all of the bone fasteners and secure connections are desirable to decrease the possibility that unanticipated and undesired stresses can cause the bone bodies or vertebrae to fracture or the screws to loosen over time. It is, therefore important that bone fastener assemblies be provided that minimize the likelihood of the establishment of undesirable stresses.

Thus, it is an object of the present invention to securely place, retain and align a rod or plate with a pedicle screw or screws over the primary longitudinal axis of the pedicle screw in order to minimize the likelihood of the establishment of undesirable stresses.

SUMMARY OF THE INVENTION

Accordingly, there is provided a threaded rod or pedicle screw for insertion into the pedicle portion of a vertebra and having at its exposed end a second threaded rod rigidly connected in a generally parallel orientation to the longitudinal axis of the pedicle screw. The second rod being offset from the longitudinal axis of the pedicle screw and having a locking pin or arm and retaining nut for affixing a rod to the pedicle screw substantially over and aligned with the longitudinal axis of the pedicle screw.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

DETAILED DESCRIPTION OF THE PREFERRED EMBODIMENTS

Figure 1:
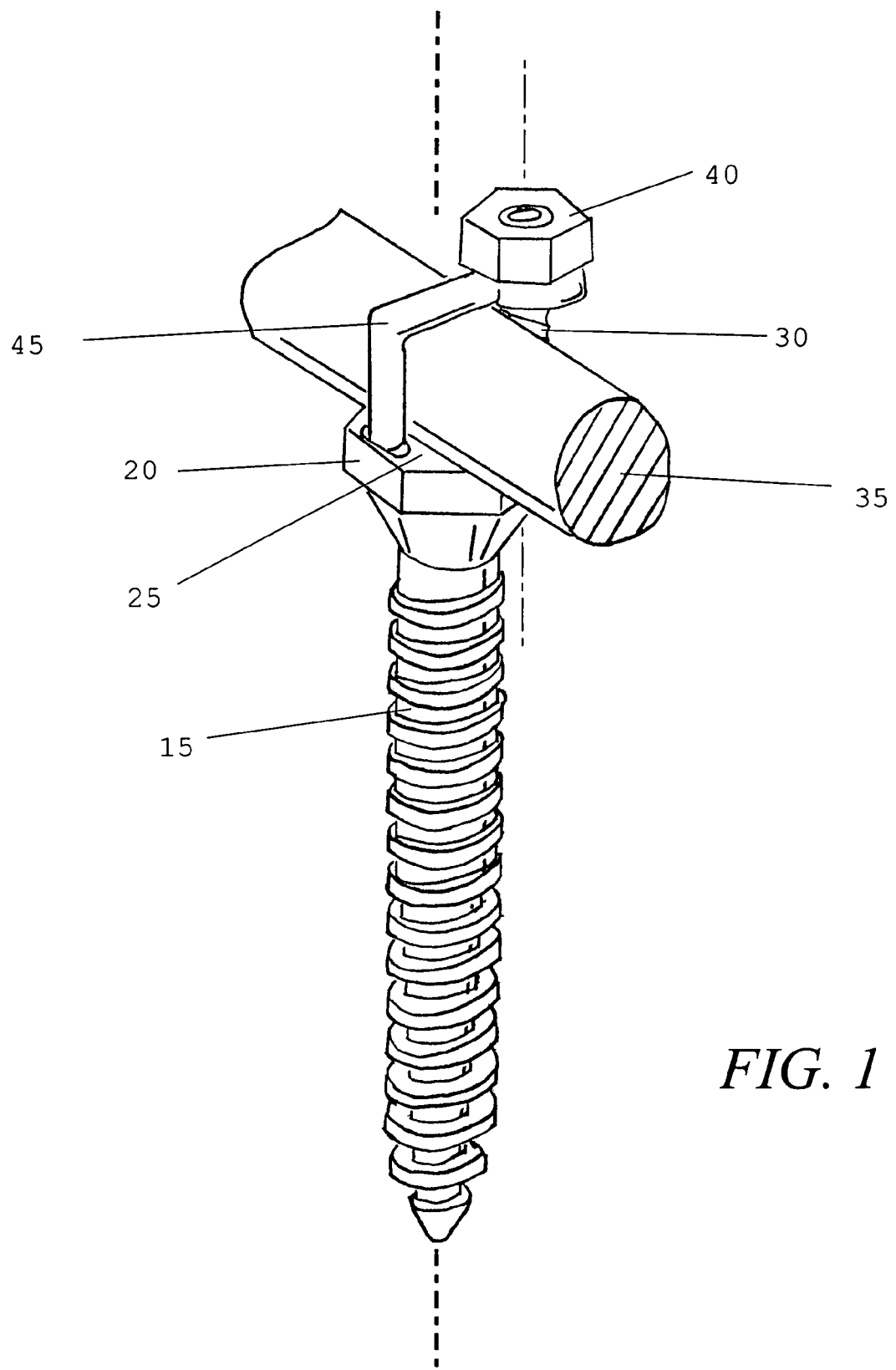
FIG. 1 is a perspective view of an embodiment according to the present invention.
Figure 2:
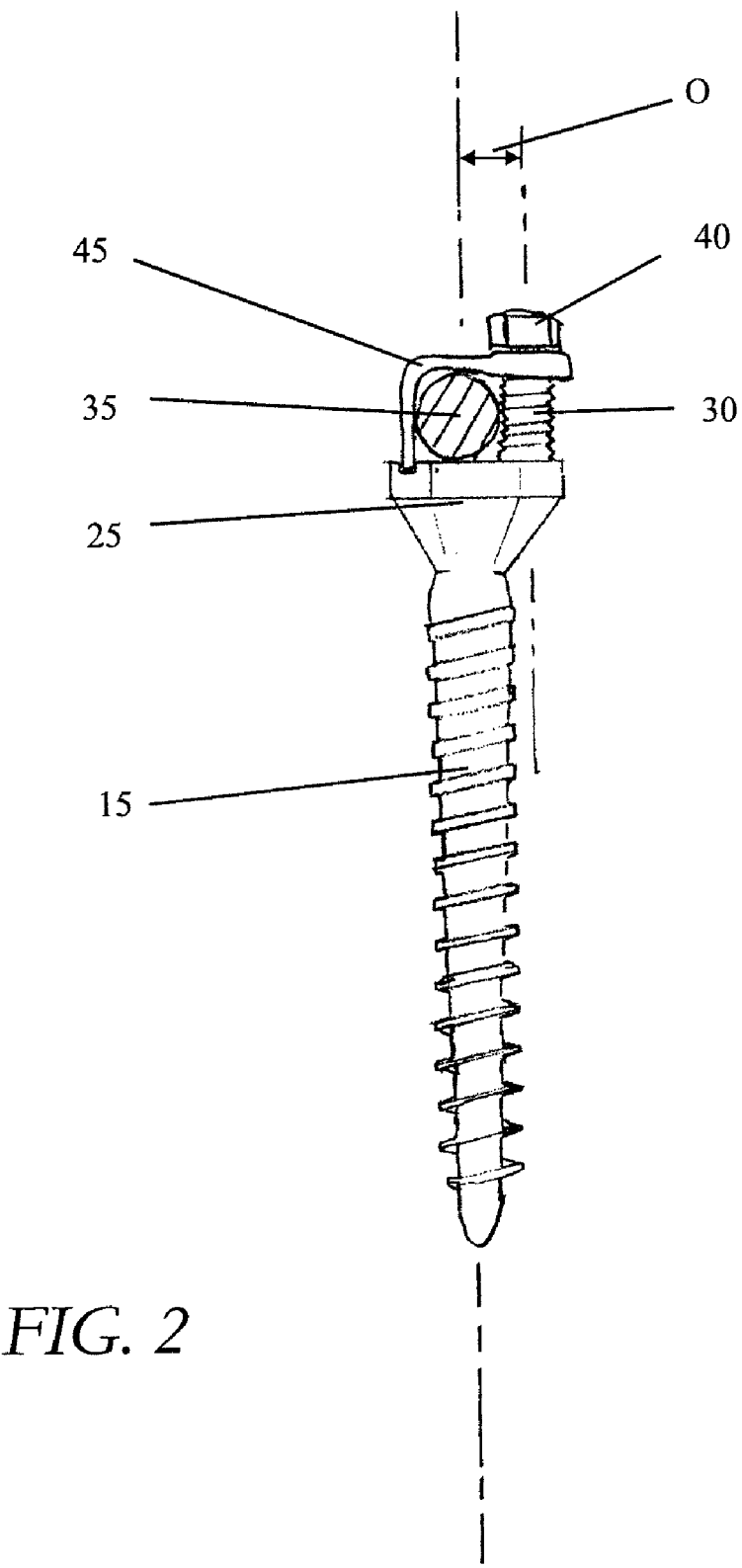
FIG. 2 is a side view of an embodiment according to the present invention.

With reference to FIGS. 1 and 2, a preferred embodiment of the present invention comprises a pedicle screw having a first threaded shaft 15 for positive engagement of the vertebra, most commonly in the pedicle region. The first threaded shaft 15 may be tapered to a penetrating point as depicted in FIG. 2 or may be of constant or stepped diameter. It should be observed that corresponding reference characters indicate corresponding parts throughout the several views of the Figures. Although the drawings represent embodiments of various features and components according to the present invention, the drawings are not necessarily to scale and certain features may be exaggerated in order to better illustrate and explain the present invention. The exemplary embodiment set out herein is illustrative of the invention and is not to be construed as limiting the scope of the invention in any manner.

In use, one end of first threaded shaft 15 is inserted into the bone while the other end remains exposed at or near the surface of the vertebra. The inserted end of the threaded shaft 15 may be coated or chemically treated to promoted bone growth and may further be provided with recesses, voids or surface textures into which bone may grow to secure the screw 15 in place.

Figure 3:
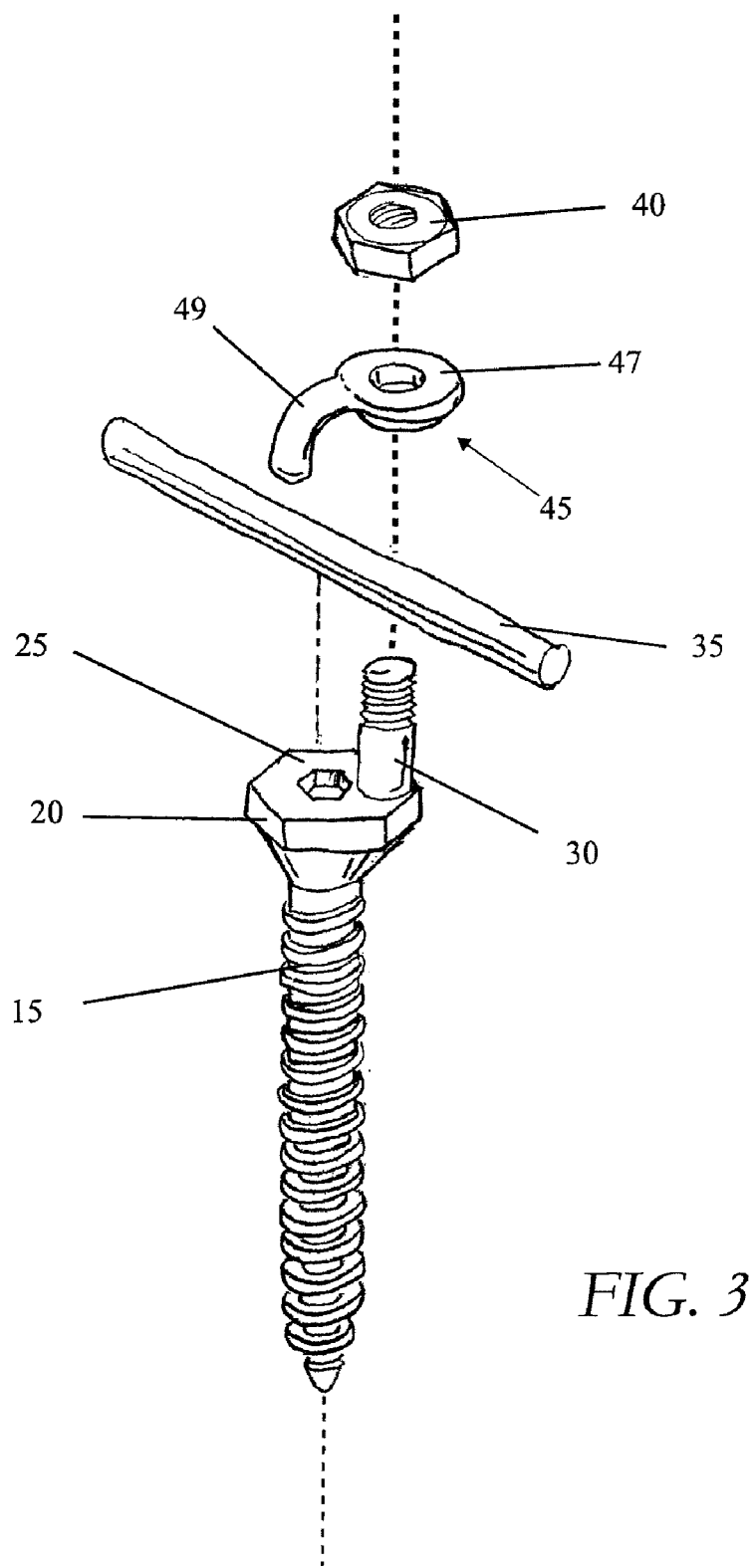
FIG. 3 is a exploded view of a embodiment according to the present invention.

A head 20 is provided at the exposed end of shaft 15. Head 20 may be at, slightly above, or slightly below the surface of the bone when inserted therein. The head 20 preferably has a hexagonal or other keyed exterior profile for positive engagement with a tool used to rotate the first threaded shaft 15 about its longitudinal axis for insertion into the bone. However, in alternate embodiments the exterior profile of head 20 may be round and a keyed (non-round) recess may be provided in the top surface of the head 20 coaxial with the longitudinal axis of the threaded shaft 15 in order to facilitate rotational insertion of the screw into the bone by insertion of a cooperative tool such as an Allen wrench into the recess, as depicted in FIG. 3.

Head 20 may have a radius equal to or greater than the maximum radius of the threaded shaft 15. Head 20 may be symmetric about the longitudinal axis of threaded shaft 15. Alternately, where head 20 is of insufficient radius to properly offset the second threaded shaft 30, as described below, head 20 may be provided with an eccentric extension sufficient to support the second threaded shaft 30 in its proper eccentric position.

Head 20 is further provided with a rod seat 25 substantially perpendicular to the longitudinal axis of shaft 15 at which a rod 35 or a portion of a plate may be engaged. The term rod or spinal rod as used herein with respect to rod 35 includes non-circular rods as well as comparable portions of spinal plates. Rod seat 25 may be shaped as to form a trough cooperative with the cross section of the rod. Where, for example, a circular rod 35 is employed a trough of similar radius may be formed in rod seat 25 in order to increase the area of contact between the rod 35 and the rod seat 25. Rod seat 25, whether or not provided with a troughed shape, may further be provided with a textured surface such as linear or diamond knurling to positively engage rod 35.

Figure 4:
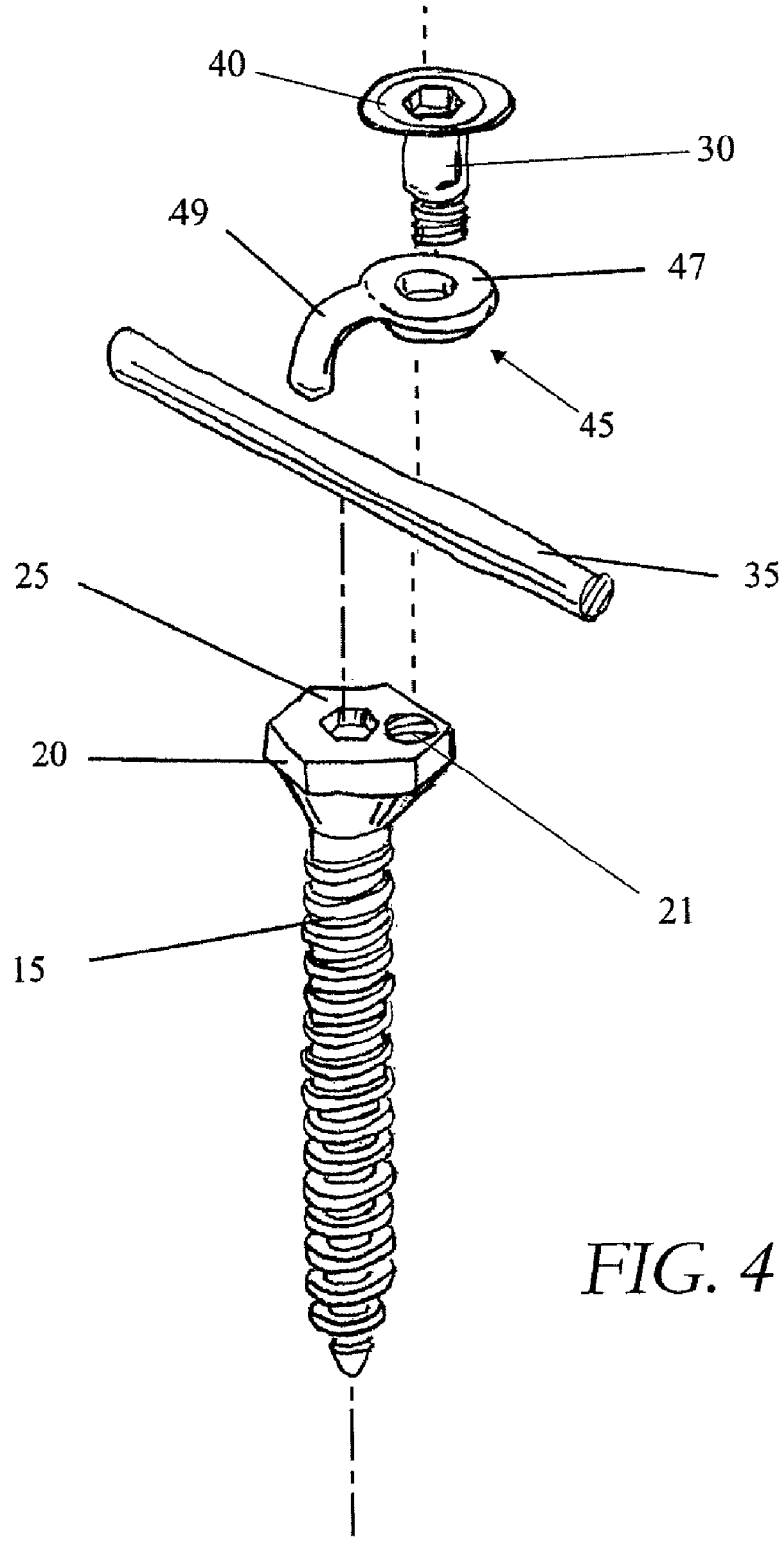
FIG. 4 is a exploded view of an alternate embodiment according to the present invention.

The second threaded shaft 30 is affixed to the head 20 eccentrically, joining the top surface of the head 20 offset from the longitudinal axis of the first threaded shaft 15 by a distance "O", as seen in FIG. 2. The second threaded shaft 30 is preferably parallel to the longitudinal axis of the first threaded shaft 15 although the second threaded shaft 30 may be angled in relation to the longitudinal axis of the first threaded shaft and may be provided with means to vary the angle prior to engagement with the rod. Second threaded shaft 30 may be integrally formed with the head 20 or may be joined to the head by any known method. In one embodiment as seen in FIG. 4, second threaded shaft 30 includes screw threads at its proximal end for threaded insertion into a corresponding internally threaded bore 21 in the head 20. Screw threads at the proximal end of shaft 30 in this embodiment are preferably of a smaller radius than the unthreaded medial portion of shaft 30 so as to create a shoulder at the transition, the shoulder abutting the surface of head 20 so as to indicate to the surgeon full engagement of the threaded portion and for support of the shaft 30. Second threaded shaft 30 may likewise be provided with screw threads at its distal end (as in FIG. 3) for engagement with a retaining nut 40. Second threaded shaft 30 may be threaded along its entire length (as in FIG. 2), smooth walled, or formed to cooperatively engage the surface of rod circular rod 35 in, for example, a hyperboloid form. Alternately retaining nut 40 may be integrally formed with second threaded shaft 30 (so as to enable engagement of the proximal threaded end with the internally threaded recess in the head 20) or may be adapted for threaded engagement with second threaded shaft 30.

The offset distance "O" of FIG. 2 is a function of the radius of circular rod 35 (R1) where O=R1−R2 and where R2 is the radius of the second threaded shaft 30. Where said second threaded shaft 30 is removably engaged with the head 20, as when provided with a threaded proximal end, a variety of second threaded shafts 30 having different radii R2 may be provided to the surgeon at the time implantation so that the surgeon may selectively vary the offset O based on the chosen circular rod 35 diameter or shape. The term "radius" used herein implies that rod 35 is a circular in section however the term is intended to encompass a like dimension of rods having non-circular sections such as elliptical or rectangular.

As best seen in FIG. 3, a locking arm 45 is provided with a collar 47 and a rod arm 49. Collar 47 is formed as a circular member with central aperture for receiving the distal end of second threaded shaft 30. In an alternate embodiment, collar 47 may be "U" shaped in order to receive second threaded shaft 30 in the void of the "U" without completely encircling the second threaded shaft 30. Rod arm 49 may be integrally joined to collar 49 and extends over rod 35 to retain it under compression force between the retaining nut 40 and rod seat 25. Rod arm 47 may be formed with two substantially orthogonal lengths merged at an elbow, as depicted in FIG. 1, or may be formed curvilinear to conform to the exterior surface of rod 35 as depicted in FIG. 3.

The distal end of rod arm 49 may be retained in a cooperative recess or aperture in head 20 to more securely retain the locking arm in position. However, it should be observed that such engagement is not required and locking arm 45 may be formed in keeping with the present disclosure without extending to contact head 20 at its distal end.

It should be understood that the disclosure may be used with a variety of pedicle screw designs and sizes. It should also be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

I claim:

1. A clamp assembly kit for attachment of a spinal rod having a radius R1 to a bone anchoring member, comprising:
   a first shaft having a threaded first end for insertion into a vertebra and a second end;
   a head affixed to the second end of said first shaft;
   a plurality of second shafts each having a different radius R2 from which a selected second shaft is selected and affixed to the head and offset from the longitudinal axis of the first shaft by a distance O where O=R1+R2; and
   a locking pin including a locking arm and an aperture, said aperture adapted for receiving said selected second shaft;
   whereby said spinal rod is compressed against said selected second shaft, and
   whereby the position of said spinal rod is variable relative to said longitudinal axis of said first shaft based on the radius of said selected second shaft.

2. The clamp assembly kit of claim 1 further comprising a nut and wherein each second shaft is further comprised of a threaded distal end for engagement with said nut, whereby said locking pin is maintained in compression against said spinal rod.

3. The clamp assembly kit of claim 1 wherein each second shaft is further comprised of a threaded proximal end; and
   said head is further comprised of a threaded recess for receiving said threaded proximal end of said selected second shaft so as to retain said locking pin in compression against said spinal rod.

4. The clamp assembly kit of claim 1 further comprising a recess in said head for receiving a distal end of said locking arm.

5. The clamp assembly kit of claim 1 wherein said head further comprises a seat contoured for cooperative engagement with said spinal rod.

6. The clamp assembly kit of claim 5 wherein said seat is textured for positive engagement with said spinal rod.

7. The clamp assembly kit of claim 1 wherein each second shaft is further comprised of an intermediate portion wherein said intermediate portion is contoured for cooperative engagement with said spinal rod.

8. A clamp assembly for connecting a spinal rod of radius R1 to a bone fastener, the clamp assembly comprising:
   a bone fastener for securing to bone, said bone fastener having a longitudinal axis;

a head affixed to the bone fastener and providing a seat for receiving said spinal rod;

a selected shaft selected from a plurality of shafts each having a different radius R2, said selected shaft affixed to the head and substantially perpendicular to said seat and said spinal rod and positioned on said head so as to be eccentric to the longitudinal axis of the bone fastener by a distance O where O=R1+R2, whereby the position of said spinal rod in a direction perpendicular to said longitudinal axis is variable relative to said longitudinal axis of said bone fastener based on the radius of said selected shaft; and a locking pin for retaining the rod in the rod seat, the locking pin further comprising a locking arm and an aperture, said aperture adapted for engagement with said shaft, whereby said spinal rod is compressed against said selected shaft.

9. The clamp assembly of claim 8 wherein said selected shaft is further comprised of a threaded distal end and wherein said clamp assembly is further comprised of a nut for engagement with said threaded distal end of said selected shaft whereby said locking pin is maintained in compression against said spinal rod.

10. The clamp assembly of claim 8 wherein said selected shaft is further comprised of a threaded proximal end and a nut at its distal end; and said head is further comprised of a threaded bore for receiving said threaded proximal end of said selected shaft so as to retain said locking pin in compression against said spinal rod.

11. The clamp assembly of claim 8 further comprising a recess in said head for receiving a distal end of said locking arm.

* * * * *